United States Patent
Heisler

[11] Patent Number: 5,843,106
[45] Date of Patent: Dec. 1, 1998

[54] ENDOSCOPIC SHAVER BLADE WITH SHARP OUTER EDGE

[75] Inventor: Gary R. Heisler, Holiday, Fla.

[73] Assignee: Linvatec Corporation, Largo, Calif.

[21] Appl. No.: 879,993

[22] Filed: Jun. 23, 1997

Related U.S. Application Data

[63] Continuation of Ser. No. 636,990, Apr. 10, 1996, abandoned.

[51] Int. Cl.$^6$ ................................................. A61B 17/32
[52] U.S. Cl. ........................................ 606/167; 606/170
[58] Field of Search .................................. 606/170, 167, 606/159, 169

[56] References Cited

U.S. PATENT DOCUMENTS

| | | | |
|---|---|---|---|
| 4,646,738 | 3/1987 | Trott | 606/170 |
| 5,160,318 | 11/1992 | Shuler | 606/170 |
| 5,364,395 | 11/1994 | West, Jr. | 606/170 |
| 5,411,514 | 5/1995 | Fucci et al. | 606/180 |

*Primary Examiner*—Michael Buiz
*Assistant Examiner*—Kevin Truong
*Attorney, Agent, or Firm*—Gene Warzecha

[57] ABSTRACT

A rotary blade assembly is provided with a stationary outer tube having a cutting window at its distal tip. The window has a curvilinear profile defined by a peripheral rim surrounded entirely by a land surface angled relative to the rim. The inclination of the land produces a sharp edge around the periphery of the window of the outer member. The curvilinear window is produced by a single step manufacturing process which creates the window opening at the same time that the land surrounding the opening is inclined.

17 Claims, 8 Drawing Sheets

ENDOSCOPIC SHAVER BLADE WITH SHARP OUTER EDGE

This is a continuation application of application Ser. No. 08/636,990, filed Apr. 10, 1996 now abandoned.

BACKGROUND OF THE INVENTION

1. Field of the Invention

The invention relates to elongated, powered surgical instruments for use in endoscopic tissue resection. More particularly, the invention relates to an instrument having an elongated inner tube rotatably situated within an elongated stationary outer tube, both inner and outer tubes having, at their distal ends, cutting apertures which cooperate to resect or otherwise affect tissue during endoscopic surgical procedures.

2. Description of the Prior Art

The use of elongated surgical cutting instruments has become well accepted in performing closed surgery such as arthroscopic or, more generally, endoscopic surgery. In closed surgery, access to the surgical site is gained via one or more portals, and instruments used in the surgical procedure must be elongated to permit the distal ends of the instruments to reach the surgical site. Surgical cutting instruments for use in closed surgery—also known as "shavers"—conventionally have a straight, elongated outer tubular member terminating at a distal end having an opening in the end or side wall (or both) to form a cutting port or window and a straight, elongated inner tubular member concentrically disposed in the outer tubular member and having a distal end disposed adjacent the opening in the distal end of the outer tubular member. The distal end of the inner tubular member has a surface or edge for engaging tissue via the opening in the outer tubular member and in many cases (but not all) cooperates with the opening to shear, cut or trim tissue. In some cases, such as burrs, the opening in the outer tube merely allows access to the tissue and does not otherwise cooperate to resect tissue. The inner tubular member is rotatably driven about its axis from its proximal end, normally via a handpiece having a small electric motor which is controlled by finger actuated switches on the handpiece, a foot switch or switches on a console supplying power to the handpiece. The distal end of the inner tubular member can have various configurations depending upon the surgical procedure to be performed, and the opening in the distal end of the outer tubular member has a configuration to cooperate with the particular configuration of the distal end of the inner tubular member. For example, the inner and outer tubular members can be configured to produce whisker cutting, synovial resection, arthroplasty burring or abrading, side cutting, meniscus cutting, trimming, full radius resection, end cutting and the like, and the various configurations are referred to generically as shaver blades. Cut tissue is aspirated through the hollow lumen of the inner tubular member to be collected via a vacuum tube communicating with the handpiece.

The aforementioned elongated surgical cutting instruments have also been produced in angled configurations in which the distal tips of the inner and outer members are aligned and offset or bent at either a fixed or variable angle from the proximal ends of the aligned inner and outer members. Examples of fixed and variable angle rotary surgical instruments are shown in U.S. Pat. Nos. 4,646,738 (Trott) and 5,411,514 (Fucci et al.), both assigned to the assignee hereof, and incorporated by reference herein. In other respects the operation of fixed and variable angle shavers is largely the same as that of the straight shavers described above.

One parameter affecting the efficiency of operation of shaver blades is sharpness of the edges of the windows. Various prior art designs are known to have differing degrees of sharpness of both the inner cutting edges and the periphery of the outer window. The present invention is concerned with the design and manufacture of an outer tubular member having a sharpened window periphery.

It is known that improved resection efficiency is achieved by sharpening the cutting edges and this is true of conventional scissors as well as endoscopic shavers although the manufacture of the latter is considerably more difficult. The smaller the included angle of the cutting edge, the sharper the edge. Clearly, below a certain limit the edge becomes too delicate to be practical. When applied to cylindrical, rotating shavers, the cutting edges on the inner member and the periphery of the outer window are the cooperating edges which should have the smallest included angles in order to produce sharp edges. However, this must be balanced with cost and speed of manufacture. In prior art designs, the outer window is sometimes formed by simply grinding or milling an opening at the distal tip of the outer tube, the opening lying in a plane angled relative to the tube axis. Thus, the outer window faces toward the end of the tube as well as toward the side. It will be understood that this process produces a generally elliptical window periphery which has a lower included angle at its proximal end and a larger included angle at its distal end. A land surface surrounds the periphery and is angled (in the cutting plane) such that the inner rim of the land defines the sharpened cutting edge of the outer member. The formation of this type of outer window could be achieved by a variety of two-dimensional through-cutting processes such as wire EDM (electrical discharge machining), ram EDM, conventional or electro-chemical grinding or milling. For certain purposes, this type of outer window may be sufficient, however, it is known that subjecting the land surface to additional processing produces a three-dimensional window shape and sharper edge. However, the additional steps required to produce such sharpness entail the use of either a tool having a complex contour or a machining process capable of complex contouring motions (e.g., a computer numerical control (CNC) machine). Additionally, practical manufacture of these devices would be hampered because simultaneous production of several blades is more difficult with such processes, if at all possible.

It is accordingly an object of this invention to produce an outer member of a shaver blade assembly in which the window of the outer member has a sharpened periphery.

It is also an object of this invention to produce a shaver blade assembly having an outer member with a sharpened window formed by a peripheral land surface angled to the window rim.

It is another object of this invention to produce a sharpened outer window with a simple process minimizing the use of complex tools and the number of required processing steps.

SUMMARY OF THE INVENTION

These are other objects of this invention are achieved by the preferred embodiment disclosed herein which is a surgical endoscopic tissue resecting instrument comprising an elongated outer tubular member, an elongated inner tubular member adapted to move within the outer tubular member and having a distal end, proximal end, a cutting means at said distal end for cutting tissue presented through said opening and a hub at said proximal end wherein said outer opening defines a laterally and longitudinally facing, generally elliptical periphery comprising a perimeter defined by the locus of all points lying in or on the surface of said cylindrical tube and on an arcuate surface having a predetermined curvilinear shape.

In another aspect the invention lies in a method of forming a window in a rotary shaver blade comprising the steps of providing a hollow tubular member having a closed, rounded end; orienting said hollow tubular member vertically; providing an arcuate surface forming means, said arcuate surface forming means for creating in another body an arcuate surface having a predetermined radius of curvature; facing said arcuate surface toward said closed, rounded end; inclining said arcuate surface at a predetermined angle; advancing and activating said arcuate surface toward said closed rounded end until said window is formed.

DESCRIPTION OF THE PREFERRED EMBODIMENT

Figure 1:
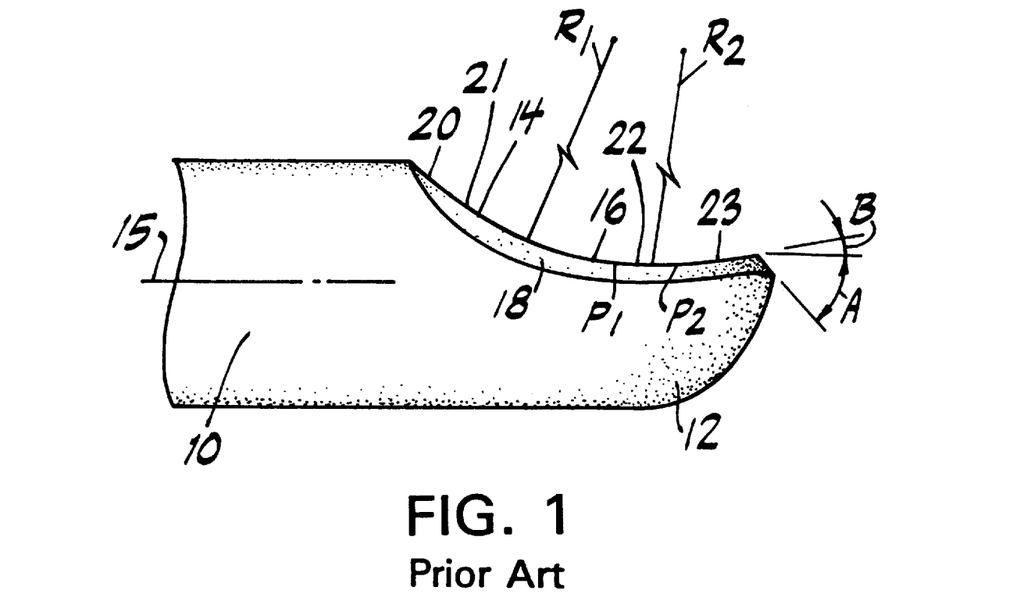
FIG. 1 is a side elevational view of the distal tip of a prior art outer tube having a curvilinear cutting window.
Figure 2:
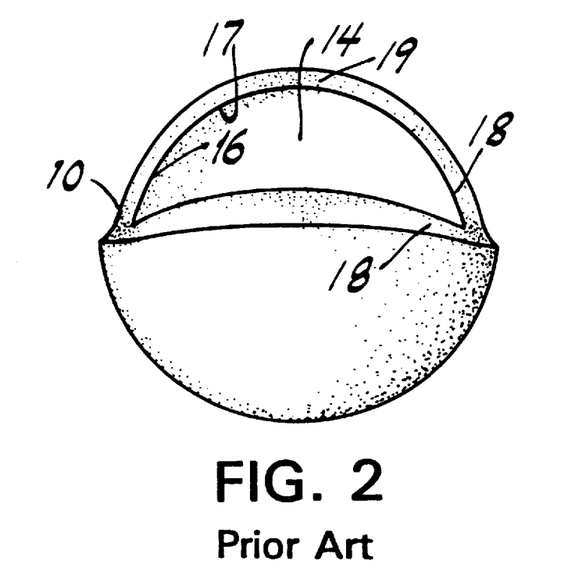
FIG. 2 is an end view of FIG. 1.
Figure 3:
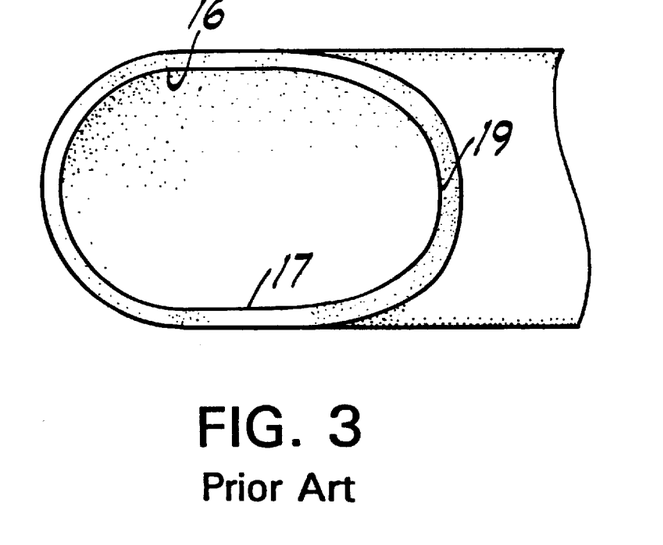
FIG. 3 is a plan view of FIG. 1.

FIGS. 1 and 2 show a distal tip of a prior art outer tubular member 10 of a rotary shaver blade assembly (not to scale). The proximal ends of the tubular member are conventional and well understood by those skilled in the art. Outer tubular member 10 has a distal tip 12 with a curvilinear cutting window 14 which faces to the side, i.e. laterally, perpendicular to axis 15, and away from the end of the blade, i.e. longitudinally in a direction parallel to axis 15. The terms "laterally" and "longitudinally" mean that the interior of the outer tubular member is visible when viewed from these vantage points. The window has a peripheral rim 16 which is formed by the intersection of the window with the interior surface 17 of the outer tube and is surrounded by a land 18 which is angled at its distal end at an angle A relative to axis 15 and the distal tip of window periphery 16. Angle A appears to be formed by a complex grinding or shaping process and appears to be uniform along the extent of the land surface. Thus, land 18 lies at angle A relative to the rim at each point along periphery 16. It is noted that proximal end 20 of window 14 is not provided with an angled land at all, thus resulting in portion 19 which is simply the end facing surface of the outer tube wall which is exposed by the cut forming window 14. The curvilinear profile of window 14 is best seen in FIG. 1 as comprising three sections: a first section 21 extending from the proximal end 20 of the window to a first predetermined point P1, and having a radius of curvature R1; a second section extending from point P1 to a predetermined point P2 adjacent the distal end of the window, this second section 22 having whatever blended radius of curvature R2 which is necessary to smoothly join the radiused section 21 to a third section 23 which is a linear portion extending at some angle B relative to axis 15. The window thus formed is best seen in FIG. 3 as having a relatively rectangular shape with rounded proximal and distal ends and generally parallel sides. Window 14 is formed by a process having at least two steps: a first step requiring passing a cutting tool through the distal tip of tube 10 along the curvilinear profile shown in FIG. 1 and a second step requiring the formation of land 18.

Figure 4:
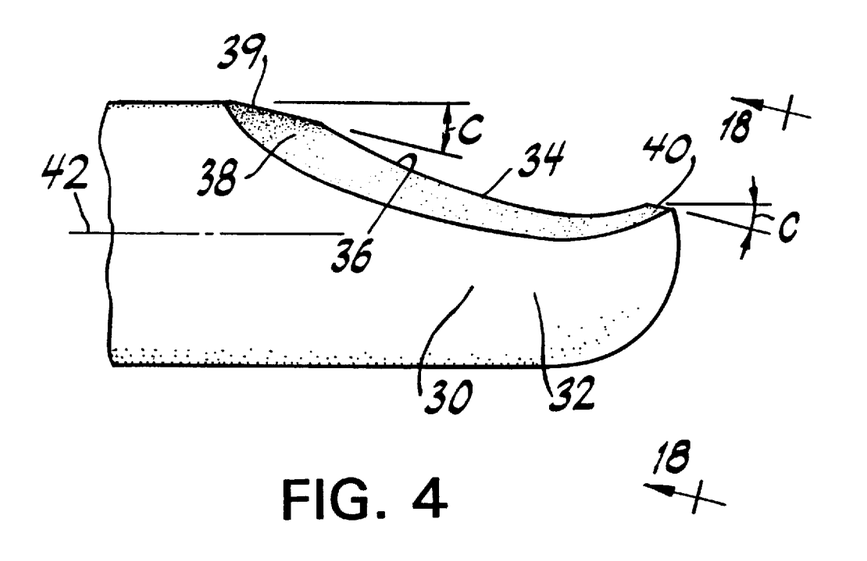
FIG. 4 is a side elevational view of a distal tip of an outer tube formed in accordance with the principles of this invention.
Figure 5:
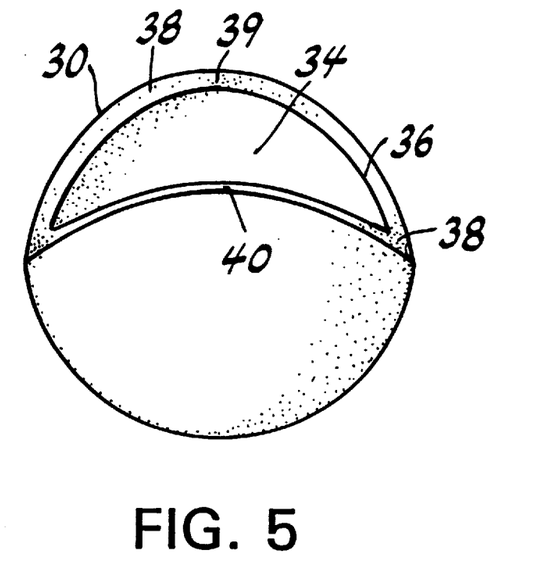
FIG. 5 is an end view of FIG. 4.
Figure 6:
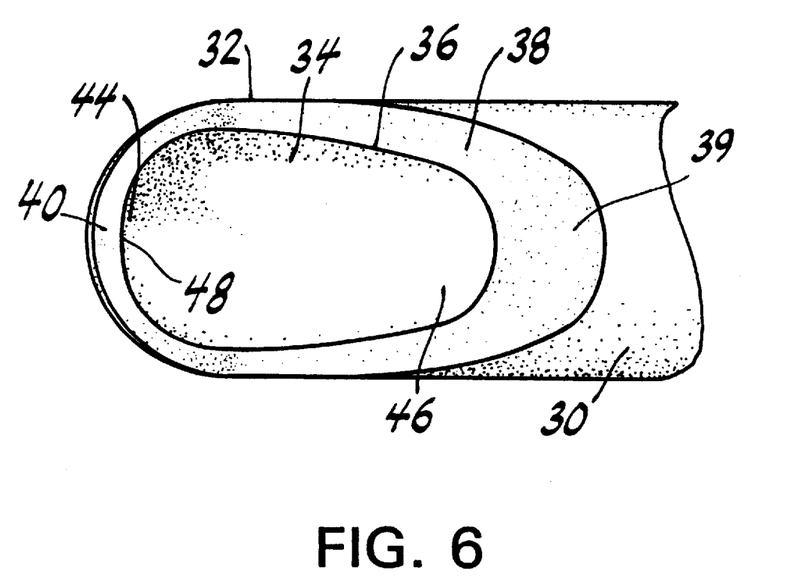
FIG. 6 is a plan view of FIG. 4.

The subject invention relates to an improved outer tube 30 and the process for forming the tube as shown in the remaining drawings. Referring to FIGS. 4 and 5, outer tube 30 has a distal end 32 provided with a curvilinear window 34 having a peripheral rim 36. The proximal end of tube 30 is conventional and forms no part of this invention. Window 34 is surrounded by a peripheral land 38 angled at its distal and proximal ends 39 and 40, respectively, at an angle C relative to the axis 42 of the outer tube. It will be noted that land 38 is, unlike the prior art embodiment discussed above, angled around the entire periphery of the window although points intermediate the distal and proximal ends 39 and 40 may be at angles other than angle C as will be understood below. As best seen in FIG. 6, window 34 is less rectangular than window 14 of the prior art embodiment and has more of a pear-shaped or generally elliptical outline with a large rounded distal end 44, a smaller rounded proximal end 46 and non-parallel sides. It should also be noted that the invention facilitates creation of a large window while maintaining a distal bearing tip 48 on axis 42. Tip 48 may act as a bearing surface against the exterior surface of the inner member.

Figure 7:
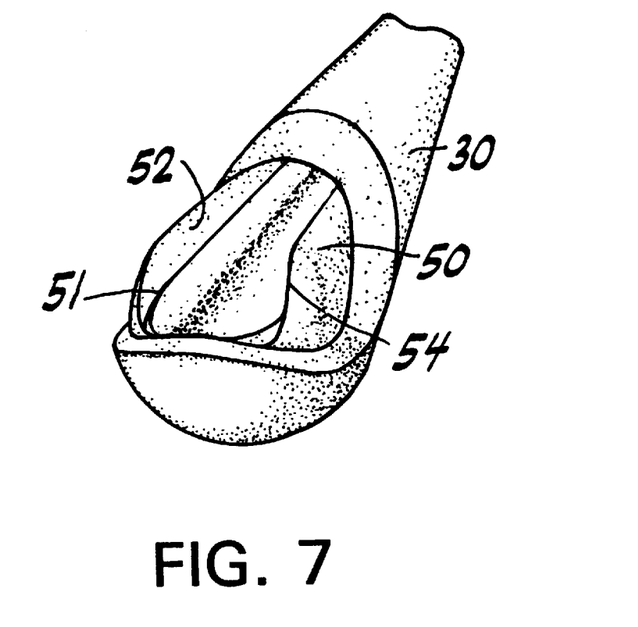
FIG. 7 is a front perspective view of the outer member shown in FIGS. 4–6 with a chosen inner member.
Figure 8:
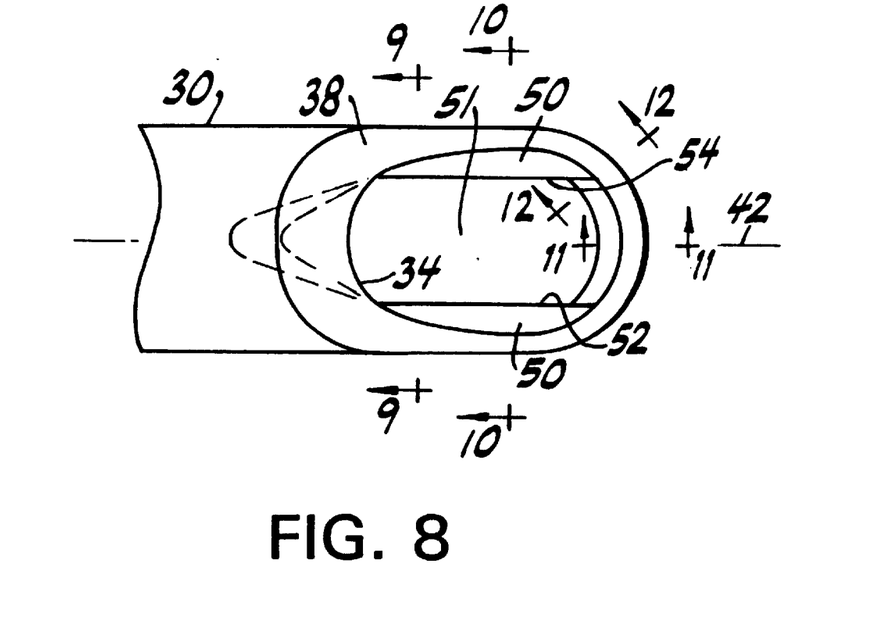
FIG. 8 is a diagrammatic plan view of FIG. 7.

FIG. 7 is a front perspective view of the distal tip of outer tubular member 30 assembled with an inner member 50 having a cutting window 51 although it will be understood that a variety of inner cutting window profiles could be used. To facilitate the explanation of the invention, FIG. 7 is presented in diagrammatic plan view in FIG. 8 showing the various points at which cross-sectional views shown in FIGS. 9 through 12 are taken.

Figure 9:
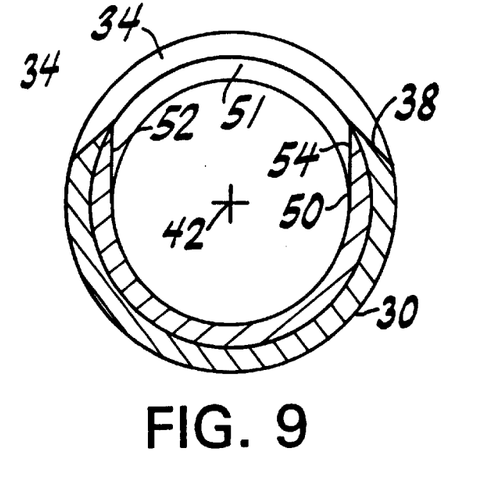
FIG. 9 is a sectional view of FIG. 8 taken along the line 9—9.
Figure 10:
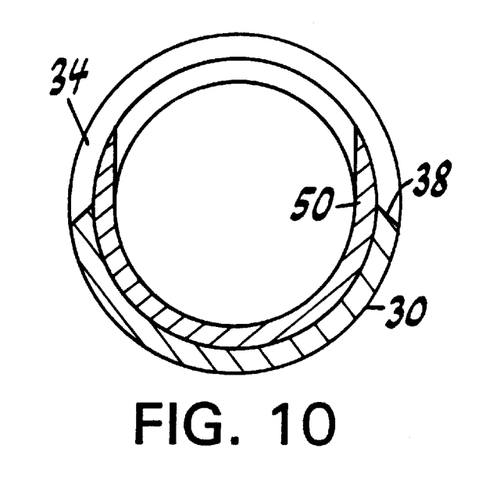
FIG. 10 is a sectional view of FIG. 8 taken along the line 10—10.
Figure 11:
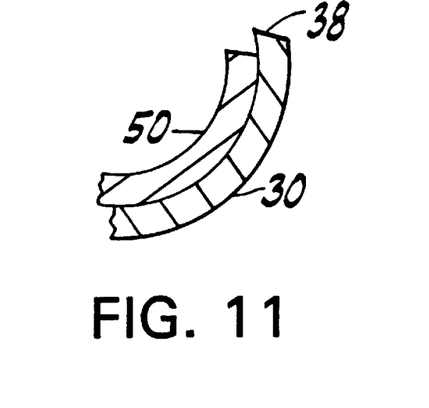
FIG. 11 is a sectional view of FIG. 8 taken along the line 11—11.
Figure 12:
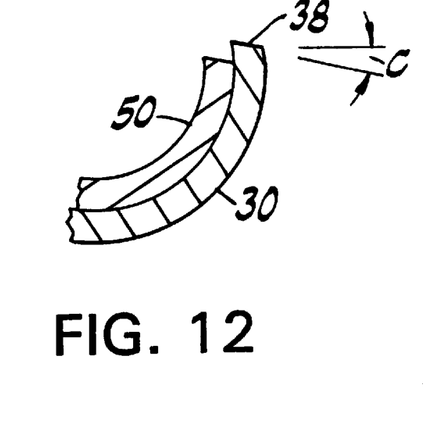
FIG. 12 is a sectional view of FIG. 8 taken along the line 12—12.

The particular form of cutting edge provided on inner member 50 has a pair of inwardly facing cutting surfaces 52 and 54 created on either side of inner window 51. Since each cutting surface 52 and 54 is close to if not exactly tangential with the interior surface of the inner tube (best seen in FIG. 10) and extends proximally from the distal tip of the inner tube, the inner window has a generally rectangular opening when viewed from the front. The inner window is formed, for example, by a wire EDM process in which the wire is longitudinally extending at a predetermined angle to the axis of the inner member and follows a generally rectangular path (viewed from the end of the tube). This path produces a tangential cutting surface at only certain points (i.e. at FIG. 10 but not at FIG. 9). The relationship of the cutting surfaces 52 and 54 relative to adjacent portions of outer window 34 is better seen by reference to FIGS. 9 through 12 which show sectional views through varying portions of FIG. 8. It will be noted that the angle of land 38 relative to a horizontal plane through axis 42 varies depending upon the longitudinal placement of the point on the land at which the angle is measured. Thus, as shown in FIG. 9, the edge of outer window 34 is fairly sharp because the wall of the outer tube is cut at a relatively low included angle compared to the angle of land 38 at other points, such as the point shown in FIG. 10. Similarly, the angle of land 38 at the point represented by FIG. 11 is different still and the angle shown in FIG. 12 is the angle C referred to above. It will be further noted that the relatively low included angle forming the cutting edge of the inner cutting window, i.e. the intersection of surfaces 52 and 54 with the outside surface of inner member 50 results in a sharp edge in the areas of FIGS. 9 and 10. The curvilinear contour of outer window 34 in combination with the sharpness of its edges along rim 36 and the edges of the inner window produces efficient tissue resection.

Figure 13:
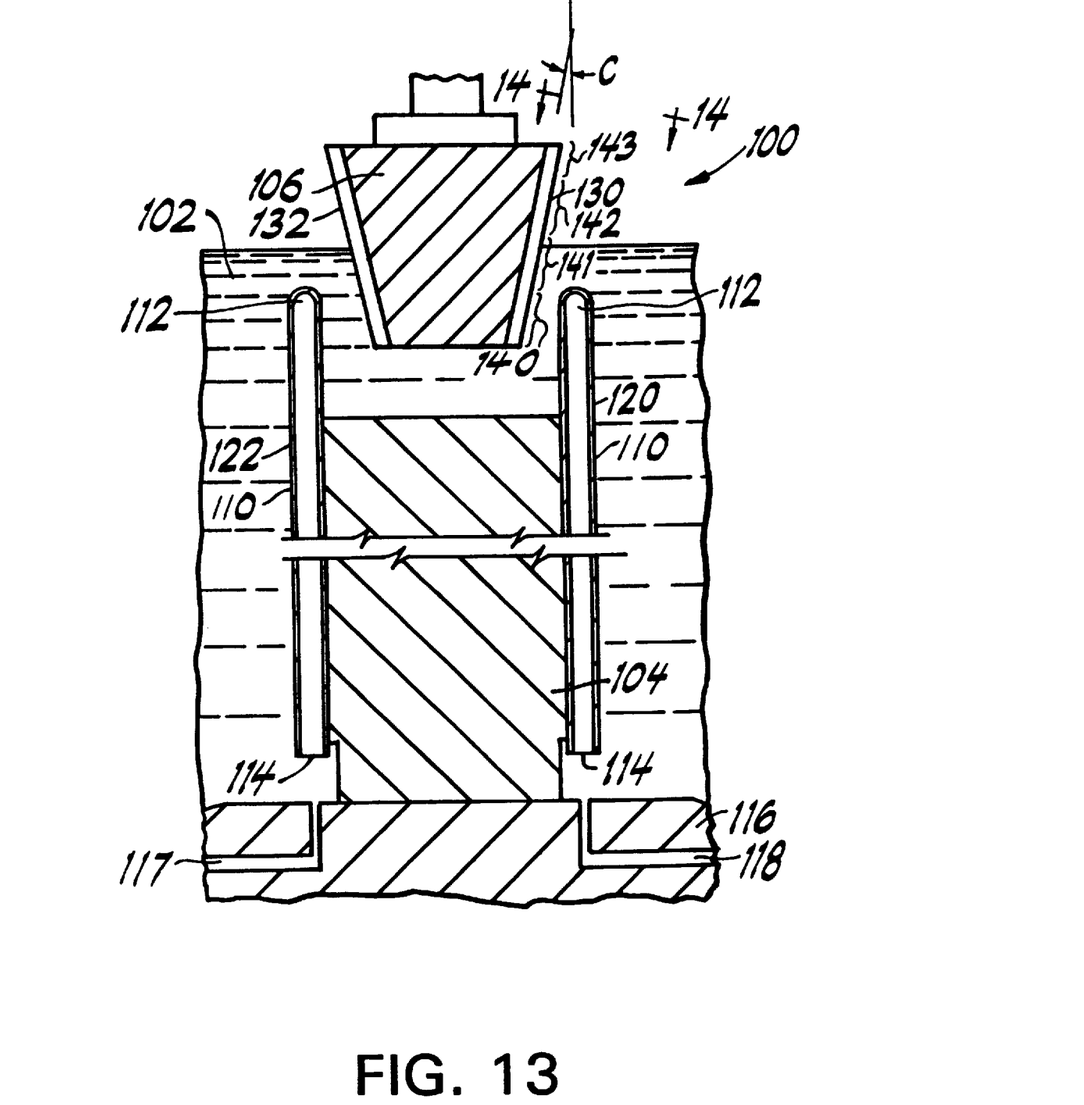
FIG. 13 is a diagrammatic elevational view in cross-section of an apparatus and method step incorporating the principles of this invention.
Figure 14:
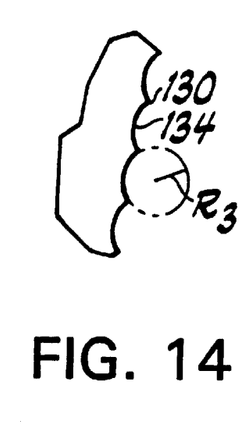
FIG. 14 is a sectional view of FIG. 13 taken along the line 14—14.

The process of forming the curvilinear contour of window 34 at the distal tip 32 is best understood by reference to FIGS. 13 through 18. The process utilizes a contouring apparatus which, in the preferred embodiment, is an electrical forming device capable of creating an arcuate surface in another body. The preferred embodiment utilizes a plunge-type conventional computer numerically controlled (CNC) EDM device 100 incorporating a basin (not shown) for holding dielectric fluid 102, a work piece holder 104 and forming electrode tool 106 mounted to the EDM upper platen. A plurality of hollow outer tubes 110 are attached in a vertical orientation to opposite sides of holder 104, each outer tube having a closed top end 112 and an open bottom end 114. Holder 104 is attached to a base 116 mounted to the EDM lower platen, the base being provided with a plurality of fluid channels 117 and 118 aligned with the open ends of associated tubes 110. While only two tubes 110 are shown in FIG. 13, it will be understood that additional tubes are arranged on holder 104 in two parallel rows 120 and 122 which may extend perpendicular to the plane of the paper. Similarly, tool 106 is in the preferred embodiment an electrode having a trapezoidal cross-section, best seen in FIG. 13, extending perpendicular to the plane of the paper and above holder 104. The angled sides 130 and 132 of tool 106 are each provided with a plurality of parallel channels 134 having arcuate profiles oriented at angle C relative to the axes of the tubes in rows 120 and 122, each having a radius of curvature R3, best seen in FIG. 14, which ultimately interacts with outer tubes 110 to create the unique profile of window 34. It will be understood that the channels could have other than circular profiles.

Figure 15:
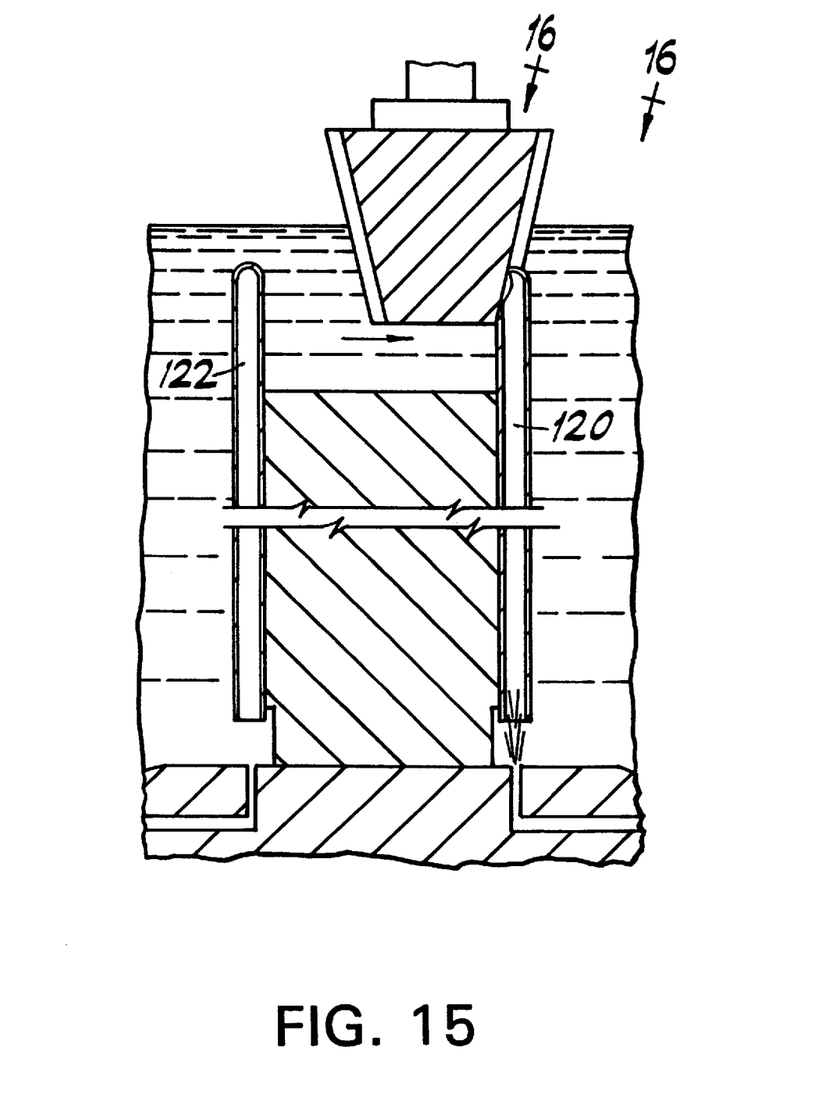
FIG. 15 is a view of the method and apparatus of FIG. 13 in a different stage of the process of this invention.

As shown in FIG. 15, electrode tool 106 is first moved down to a selected level between the parallel rows 120 and 122 of outer tubes 110 and then laterally toward one of the rows, the rate being determined by the machine control parameters in order to have the distal tip of outer tubes 110 contact a channel 134. While a plurality of channels are provided on each surface 130 and 132, not all portions of all channels need to be used at any one time and the tool may be shifted around by proper programming of the CNC machine to utilize selected portions of the channels and selected channels as will be understood below. For example, any given channel 134 may be thought of as having a plurality of adjacent sections 140, 141, 142 and 143. The vertical positioning of electrode 106 could be, for example, set to have lower-most section 140 be the active section. As the electrode continues to move laterally a predetermined distance to a selected point, the EDM process forms an opening in each of the outer tubes while dielectric fluid is flushed through channels 118 and out the opening created at the distal tip. During machining, electrical discharge parameters are modified under program control so as to minimize cycle time while maintaining acceptable surface finish and edge sharpness on the finished product. The pressurized dielectric fluid introduced by the timed flushing port reduces the machining time by removing swarf from the machining zone. The opening is defined by the intersection of the cylindrical tube wall at the rounded, closed end of the tubes with the arcuate profile of channels 134.

When the tool has been moved laterally a programmed distance to form the desired window 34, the direction of the tool is reversed to approach row 122 and the channels along surface 132 are brought into engagement with the outer tubes in row 122 in order to produce the chosen profiles in those tubes.

Figure 18:
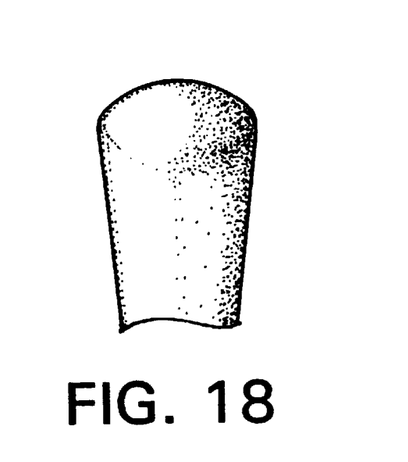
FIG. 18 is an end view of FIG. 4 taken along the line 18—18 showing the profile of the tip viewed along a line angled relative to its axis.

It will be appreciated by those skilled in the art that while tool 106 has a relatively simple shape and moves in a relatively simple pattern, the intersection of the tool with the outer tube produces a resultant complex profile. Rather than being defined by a complex shape requiring several processing steps for its formation, the window 34 has a simple arcuate profile when viewed in FIG. 16, or better still, when viewed along a line at an angle C to the tube axis as best seen in FIG. 18. The intersection of the arcuate channel profile with the cylindrical tube results in cutting edges with low included angles thereby making a subsequent sharpening operation unnecessary.

The shape of the surface of any given land 38 surrounding rim 36 and the shape of the associated actual window 34 may be considered as being defined by the locus of all points lying at the intersection of an elongated, transversely arcuate surface with the cylindrical body of the tube oriented at a predetermined angle relative to the transversely arcuate surface. Put another way, the definition of the perimeter of window 34 may be thought of as the intersection of a cylindrical body with an imaginary surface having a predetermined, symmetrical, concave arcuate profile. In practice this imaginary surface is defined by the concave surface of channel 134 and is considered endless because the surface extends entirely through the cylindrical body enough to form a window therein. In the preferred embodiment, however, the activatable sections (140, etc.) of the surface of channel 134 lie on this imaginary surface and need only subtend a lateral or transverse distance approximately greater than or equal to one-half the outside diameter of the cylindrical body in order to form land 38. If the imaginary surface is linearly extended in a direction which is aligned with the axis of the tube, and if the arcuate profile transverse to the axis is a simple concave radius, the resultant locus of points defines convex land 38 (complementary to the concave radius). If some other orientation or profile is used, the locus of points will produce a different shape.

Figure 16:
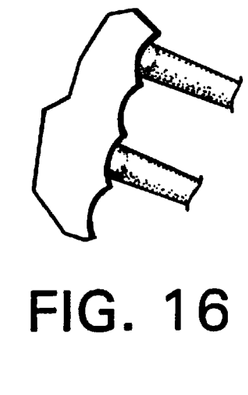
FIG. 16 is a sectional view of FIG. 15 taken along the line 16—16.
Figure 17:
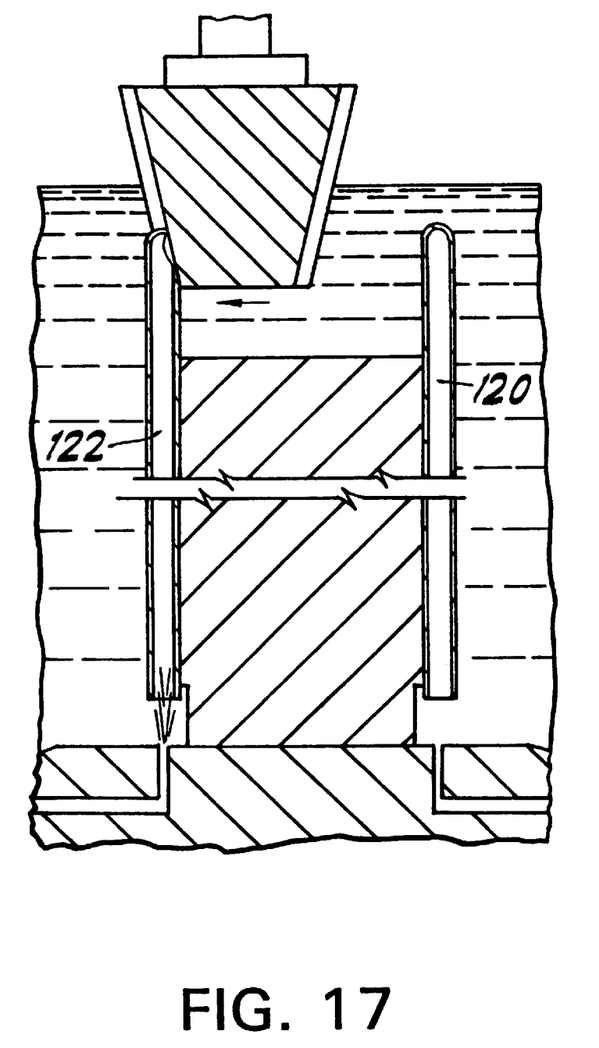
FIG. 17 is a view of FIG. 15 taken at a different stage in the process of the invention.

The transverse curvature of window 34 when viewed as shown in FIG. 16 is the same as that shown in FIG. 18.

While the arcuate profiles of channels 134 are at a constant radius of curvature along the length of the channels, it will be understood that the radius of curvature may vary along the channel length and/or the arcuate surface may have a contour other than circular extending along the axis line.

Because the shape is two-dimensional when viewed axially to the cylindrical surfaces 130 and 132 of the tool, complex shaped tooling or simultaneous programmed machine motions are not required. The shape may be machined by using CNC wire EDM, or produced by conventional or electrochemical grinding using a wheel onto which the proper radius has been dressed. Similarly, plunge type EDM or ECM may be used with the part contour being produced by contours on the tooling. Tooling cost is low due to the simple profile and, because complex machine motions are not required, simultaneous multiple part machining is readily implemented.

It will be understood by those skilled in the art that numerous improvements and modifications may be made to the preferred embodiment of the invention disclosed herein without departing from the spirit and scope thereof.

What is claimed is:

1. A surgical endoscopic tissue resecting instrument comprising:

an elongated outer tubular member comprising a cylindrical body having an axis, an outer surface, a distal end, a proximal end and an opening at said distal end wherein said opening defines a laterally and longitudinally facing, generally elliptical periphery, in plan view, comprising a perimeter and a surrounding surface defined by the locus of all points lying at the intersection of said cylindrical body and an imaginary, elongated arcuate surface which is endless and passes through said cylindrical body, said imaginary surface being linear at all of its points aligned in a lengthwise direction and having a predetermined transverse curvilinear shape; and an elongated inner tubular member adapted to move within said outer tubular member and having a distal end, proximal end and a cutting means at said distal end for cutting tissue presented through said opening.

2. A surgical instrument according to claim 1 wherein said surrounding surface comprises a land entirely surrounding said opening and inclined relative to the outer surface of said cylindrical body of said outer tubular member.

3. A surgical instrument according to claim 1 wherein said distal end of said outer tubular member comprises a distal tip for providing a bearing surface against the exterior of said inner tubular member distal end.

4. A surgical instrument according to claim 1 wherein said imaginary, elongated arcuate surface extends along and is symmetrical to a predetermined axis and wherein said predetermined axis is inclined at a predetermined angle relative to said axis of said cylindrical body.

5. A surgical instrument according to claim 4 wherein said predetermined axis of said imaginary, elongated arcuate surface intersects said cylindrical body axis at a point distal to said distal end of said outer tubular member.

6. A surgical instrument according to claim 4 wherein said imaginary, elongated arcuate surface has a concave surface which faces said cylindrical body.

7. A surgical instrument according to claim 1 wherein said imaginary, elongated arcuate surface has an axis coplanar with said axis of said cylindrical body and wherein said imaginary, elongated arcuate surface extends distally relative to said cylindrical body, at a predetermined angle between said axis of the cylindrical body and said axis of the imaginary, elongated arcuate surface, such that said axis of said imaginary, elongated arcuate surface passes through said cylindrical body from a predetermined first point on said outer surface of said cylindrical body to a predetermined second point on said axis of said cylindrical body, said predetermined second point distal to said distal end of said cylindrical body.

8. A cutting tip for a tubular member of a shaver blade assembly comprising:

a cylindrical tube having an axis, a closed end and an opening in the side and end defined by the locus of all points lying at the intersection of said cylindrical tube and an imaginary, elongated arcuate surface which is endless and passes through said cylindrical tube, said imaginary surface being linear at all points aligned in a lengthwise direction and having a predetermined transverse curvilinear shape.

9. A cutting tip according to claim 8 wherein said imaginary, elongated arcuate surface extends parallel to a predetermined axis line and wherein said axis line is inclined at a predetermined angle relative to the axis of said cylindrical tube.

10. A method of forming a window in a shaver blade comprising the steps of:

providing a hollow tubular member having a distal end;

providing an elongated arcuate surface forming means comprising a first elongated arcuate concave surface which is linear in the direction of elongation and which has a predetermined transverse curvilinear shape for, upon operation thereof, creating in said hollow tubular member at least one second arcuate convex surface complementary to a predetermined portion of said first arcuate surface;

orienting said first arcuate concave surface at a predetermined orientation relative to said hollow tubular member; and advancing said first arcuate concave surface toward said end and operating said first arcuate concave surface to cause it to remove a predetermined portion of said hollow tubular member to create in said hollow tubular member a window defined by the intersection of said hollow tubular member and said first arcuate surface.

11. A method according to claim 10 wherein said elongated arcuate surface forming means is an electrode component of an electrical forming device and wherein said first elongated concave arcuate surface comprises an activatable electrode surface thereof.

12. A method according to claim 10 wherein said first arcuate surface is elongated in a first direction and wherein a transverse cross-section of said first arcuate surface in a plane perpendicular to said first direction comprises, at all operative points along the length of said first arcuate surface, a curve having a predetermined radius of curvature.

13. A method according to claim 12 wherein said transverse cross-section is the same at all points along the length of said first arcuate surface.

14. A method according to claim 10 wherein said distal end of said hollow tubular member has an axis and wherein said step of orienting further comprises:

positioning said first arcuate surface at a predetermined angle relative to said axis of said distal end of said hollow tubular member such that at least one longitudinally extending imaginary line, parallel to said axis and lying on said first arcuate surface will, upon formation of the window, intersect said axis at a predetermined point distal to said distal end of said hollow tubular member.

15. A method according to claim 14 wherein said first arcuate surface is symmetrical about a line of symmetry and wherein said line of symmetry intersects said axis at a predetermined point distal to said distal end of said hollow tubular member.

16. A surgical endoscopic tissue resecting instrument for attachment to a handpiece comprising:

an elongated outer tubular member comprising a cylindrical body having an axis, a distal end, a proximal end, an opening at said distal end and a hub at said proximal end for attaching same to a handpiece, wherein said opening defines a periphery comprising a perimeter and a surrounding surface defined by the locus of all points lying at the intersection of said cylindrical body and an imaginary, elongated arcuate surface, said imaginary surface being endless and linear at all of its points aligned in a lengthwise direction and having a predetermined curvilinear shape transverse to its length; and an elongated inner tubular member adapted to move within said outer tubular member and having a distal end, proximal end, a cutting means at said distal end for cutting tissue presented through said opening and a hub at said proximal end for attaching same to a handpiece.

17. A surgical instrument according to claim 16 wherein said distal end of said outer tubular member is at least partially closed by a radially inwardly extending portion of said cylindrical body.

* * * * *